United States Patent [19]
Clarke

[11] 4,052,162
[45] Oct. 4, 1977

[54] MONITORING DEVICE

[75] Inventor: John Robin Paul Clarke, Runcorn, England

[73] Assignee: Imperial Chemical Industries Limited, London, England

[21] Appl. No.: 672,627

[22] Filed: Mar. 31, 1976

[30] Foreign Application Priority Data
Apr. 8, 1975 United Kingdom .............. 14317/75

[51] Int. Cl.$^2$ ...................... G01N 21/12; G01N 31/22
[52] U.S. Cl. ............... 23/253 R; 23/254 R; 23/255 R
[58] Field of Search ............. 23/253 R, 254 R, 255 R, 23/232 R

[56] References Cited
U.S. PATENT DOCUMENTS

| | | | |
|---|---|---|---|
| 2,227,117 | 12/1940 | Woodson | 23/254 R |
| 2,345,090 | 3/1944 | Brace | 23/255 R X |
| 2,551,281 | 5/1951 | Moses et al. | 23/255 R |
| 2,812,243 | 11/1957 | Goody | 23/255 R |

Primary Examiner—Robert M. Reese
Attorney, Agent, or Firm—Cushman, Darby & Cushman

[57] ABSTRACT

A monitor for fluids comprising a pump adapted to convey a fluid sample from the exterior of the monitor into contact with a portion of an indicator tape, a transport mechanism for advancement of the tape to expose a fresh portion of the tape to the fluid sample, and a single electric motor adapted to drive both the pump and the tape-transport mechanism.

4 Claims, 4 Drawing Figures

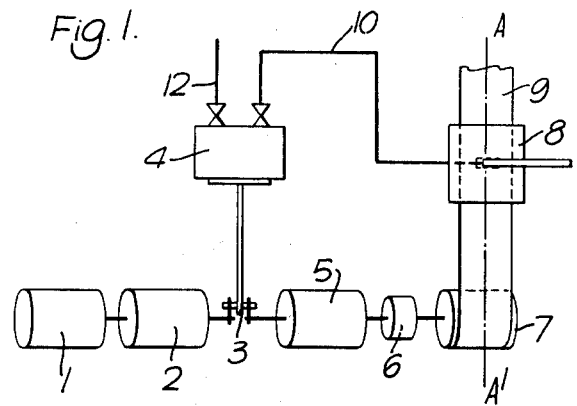
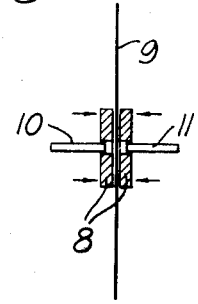
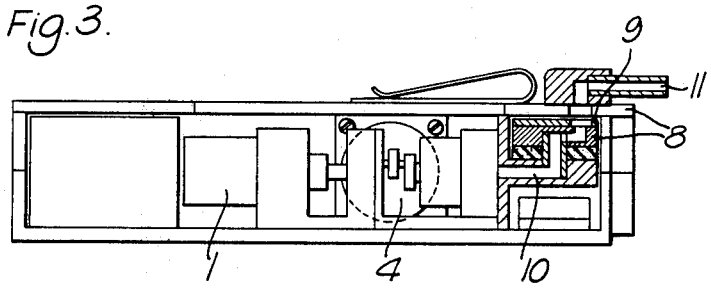
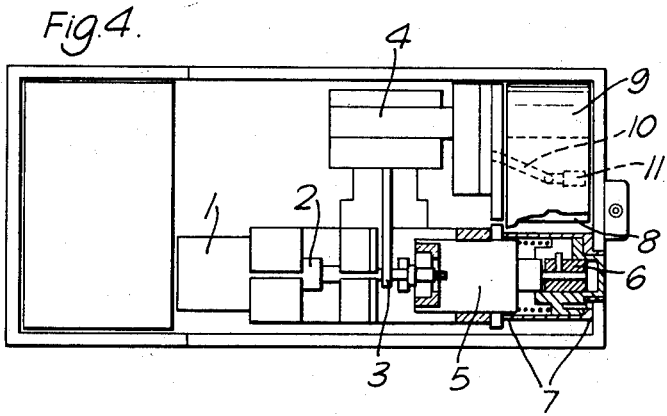

MONITORING DEVICE

This invention relates to apparatus for monitoring fluids and in particular to a device for monitoring fluids by means of an indicator tape.

It is known to monitor fluids, especially gas, and in particular to monitor toxic or noxious components of fluids, by causing a sample of the fluid to contact a tape impregnated with a substance which traps the fluid component to be monitored. Usually, but not necessarily, the substance which traps the fluid component will be an indicator which undergoes a colour change when exposed to the fluid component being monitored so that the tape becomes stained. Generally, a porous tape is employed, for example a paper-tape, and a sample of the fluid to be monitored is passed through the tape. Monitoring devices based on the above principle are known which comprise a pump for passing a fluid sample into contact with and/or through the tape and means for advancing the tape either continuously or intermittently to expose a fresh area of the tape to the fluid. An electric motor often is provided for driving the pump and a separate electric motor may be provided for driving the tape-advancement mechanism.

A single power source, for example a battery, may be used to drive both motors.

We have found that whilst the known monitoring devices are effective in detecting the presence of toxic or noxious fluid components qualitatively, they tend to be unreliable for quantitative estimation of components of fluids. In theory, knowing the mean flow rate of fluid from the pump and the speed of advancement of the tape, it is possible from the density of stain produced on the tape to calculate the concentration of the fluid component causing the stain, over any period for which the tape was exposed to the fluid. However, any changes in the relative speeds of the two electric motors, caused for example by loss of efficiency of one of the motors or its associated gearings, could result in an incorrect quantitative estimation of the concentration of the fluid component; two speed-regulators might be provided to try to ensure a constant relationship between pump and tape speeds, but this increases the size and particularly the expense of the monitor. Furthermore, the known monitors tend to be relatively large, heavy and expensive owing to the need to provide two electric motors each with its associated electrical circuitry, and, gears, etc. Consequently they are not very suitable for use as portable monitors and particularly not as personal monitors of the type which can be carried in or clipped on to a person's pocket.

We have now devised a monitor of the type described above wherein the above disadvantages are overcome to a large extent and which in a preferred embodiment is a small, lightweight, personal monitor.

According to the present invention there is provided a monitor for fluids comprising a pump adapted to convey a fluid sample from the exterior of the monitor into contact with a portion of an indicator tape, a transport mechanism for the tape and a single electric motor adapted to drive both the pump and the tape-transport mechanism.

The monitor may be of a variety of different types and sizes, for example it may be a comparitively large bench-mounted or panel-mounted monitor used in a fixed location, but in the preferred embodiment it may be a small portable monitor. In a portable monitor every component is fitted into a small case and made as light as possible and a power source, for example a small battery is usefully incorporated in the same case. It is in the small portable monitor where the invention shows the greatest advantage because the provision of a single motor and power source saves space and weight and also, in general, results in less power usage than two motors each performing a different function. Other advantages will be discussed below.

The fluids normally monitored by means of an indicator tape are gases or vapours, often toxic or noxious gases or vapours, and a particular use of the monitoring device is for detecting hazardous conditions caused by the presence of toxic gases in the atmosphere. Because a single electric motor and power source is provided, a constant relationship is ensured between pump and tape speeds so that the used tape can be employed to calculate reliably the concentration of the fluid component being monitored over a period for which the tape was exposed to the fluid. Exposure to critical levels of toxic components can be detected rapidly and appropriate action taken.

The pump is required to transport the fluid sample, usually a gas, from the sampling area (which may be for example the atmosphere surrounding the device or a gaseous sample in a container) and bring it into contact, with, and preferably cause it to pass through the indicator tape. The indicator tape normally will be porous (e.g. a paper) tape impregnated with one or more chemical compounds which will undergo a colour change when exposed to one or more particular components of the fluid being monitored. Indicator compounds are known for many toxic gases, for example, oxides of nitrogen, phosgene, hydrogen sulphide or cyanide and chlorine. Gases which themselves cannot be detected directly may be converted by an appropriate pretreatment into gases which can be detected directly; for example vinyl chloride for which an indicator is not known may be oxidised to chlorine gas for which an indicator is known. Thus, for example, a tube containing an oxidising agent may be connected to the fluid inlet port to the monitor so that a fluid containing vinyl chloride is drawn through the oxidising agent to produce chlorine for detection in the monitor.

It is usual to employ a porous tape which will allow passage of the fluid sample through the pores and so expose a large surface area of the indicator compound to the fluid and also provide the maximum contact between the fluid and the indicator compound. Accordingly it is preferred to use a pump in this invention which is capable of generating a small pressure differential across the tape sufficient to cause the fluid to pass from one side of a porous tape to the other. A suitable form of pump is a diaphragm pump, but other types may be used if desired.

The electric motor is also used to drive the transport mechanism for the tape. It is usual to advance the tape in one direction only over a period of time, either continuously at a uniform speed or in successive steps at predetermined intervals of time so that fresh portions of tape are brought into contact with the fluid sample.

There is a major advantage in using the same electric motor to drive both tape and pump in that over any given period of time a predetermined, definite ratio will exist between the volume of fluid contacting the tape and the length of tape exposed to the fluid. This ratio may be changed be appropriate selective gearing in drive couplings from the motor to each component of the device.

Thus whatever the speed of the motor (and a variable speed motor may be employed with advantage so that a variety of sizes of gaseous sample may be handled in unit time) the number of strokes of the pump (and hence for a positive displacement pump the volume of gaseous sample employed) may be calculated simply by reference to the length of tape exposed and a reliable quantitative analysis of the tape is possible.

As stated hereinbefore, a particularly suitable form of pump is a diaphragm pump. Using such a pump contact of the fluid sample with the indicator tape preferably is on the inlet stroke of the pump between the fluid inlet port of the monitor and the pump chamber.

Discharge of fluid from the pump may be inside or outside the case of the monitor. Discharge of fluid inside the monitor case may be advantageous in creating a slightly greater pressure inside the monitor than outside it, and this, together with the slight increase in pressure inside the monitor caused by movement of the diaphragm on the suck stroke of the pump, ensures that undesirable leakage of fluid into the monitor through any imperfect seals in the monitor case is inhibited. Providing the fluid component being monitored has reacted fully with the indicator compound on the tape, discharge of the spent fluid inside the monitor case will not affect the amount of fluid trapped by the tape or the density of the stain produced on the tape.

As explained above one or more tubes containing treating agents may be connected to the fluid inlet port of the monitor for pretreatment of the fluid sample. For example vinyl chloride may be oxidised to yield chlorine for detection, using a conversion tube containing a known oxidising agent.

If desired one or more conversion or other pretreatment tubes may be incorporated in the monitor caseing, although they may be connected externally to the fluid inlet port as and when required.

The monitor produces a tape upon which the fluid component being monitored is trapped. In a preferred embodiment of the monitor, a tape is employed on which the substance trapping the fluid component is an indicator which changes colour on exposure to the fluid component so that the used tape bears a stain, the density of the stain depending upon the concentration in the fluid sample of the component causing the stain, and upon the exposure time. The density of the stain may be assessed by eye against standard reference stains, either immediately or at some later time when the tape has been removed from the monitor and unwound from the winding drum. Visual examination of the tape by eye may be adequate in many instances, for example if it is simply required to ensure that a critical exposure level of a toxic gas is not exceeded, but if desired or if an accurate analysis is required, the stain may be assessed by an optical instrument. Such an instrument may be built into the monitor if desired, particularly in larger versions of the monitor intended for bench or wall mounting, and if required they can be coupled with visual and/or sound-emmitting alarm systems, to indicate, for example, when critical concentration levels of toxic gases in the atmosphere are reached or approached; the hazard indicated may be a health, fire, explosion or other hazard, as desired.

In cases where the substance used to trap the fluid component is not an indicator which undergoes a colour change, the used tape may be analysed by, for example, chromatographic or spectral analysis, or it may be treated with a substance which causes a colour stain to be developed.

A preferred embodiment of the monitor, a personal instrument, is shown in the accompanying drawings, in which:

FIG. 1 is a line diagram showing the inter-relationship of the component parts of the monitor, FIG. 2 is a section along the line A-A$^1$ shown in FIG. 1, indicating the location of the tape between plates and fluid ports, FIG. 3 shown a side view with the side plate removed of the component parts fitted into a pocket-size case, and FIG. 4 shows a plan view of the monitor with the cover plate removed.

Referring to FIGS. 1 and 2, a motor 1 and gearbox 2 are connected by a crank and connecting rod mechanism 3 to a reciprocating diaphragm pump 4. A speed reduction gearbox 5, connected directly to the crank mechanism 3, is connected to a tape-winding drum 7 via a clutch 6. The tape 9 is passed between a pair of plates 8 (which are resiliently biassed together, for example by springs, magnets or elastic bands not shown in the drawings) and attached to the winding drum 7. Each of the plates 8 is perforated with a single hole and the plates are brought together so that the holes are concentric as shown in detail in FIG. 2. The pump inlet is connected to the hole in one of the perforated plates by tube 10: the other perforated plate has a fluid inlet port 11 making contact with the hole therein. The fluid inlet port is adapted to make connection to a sampling chamber or to a drying tube or an absorption tube for pre-conversion of an undetectable substance into a detectable substance.

When the motor 1 is powered it drives the crank mechanism 3 and pump 4 via the gearbox 2. At the same time the motor also drives the tape-winding drum 7 via the gearbox 5 and clutch 6 and so is able to move the tape 9 between the perforated plates 8. The pump 4 pulls the fluid sequentially through the inlet port 11, the first plate, the tape 9, the second plate and tube 10 before exhausting it from the pump outlet 12. The tape is made of porous paper chemically treated so that those components of the fluid it is desired to monitor, in passing through the tape, are trapped and give rise to a stain on the tape.

The arrangement of the component parts fitted into a case of dimensions only 132 × 62 × 38 mm is shown in FIGS. 3 and 4. FIG. 3 is a side view showing the interior of the device with the side of the case removed and FIG. 4 is a view showing the internal layout with the upper plate of the case removed. The reference numerals are used in FIGS. 3 and 4 to denote the same component parts as those used in FIGS. 1 and 2. The monitor is particularly suited to use as a personal monitor for toxic gases which can be conveniently carried e.g. in a breast pocket or attached by a clip (see FIG. 3) to clothing when a person is working in, or is proposing to enter, a potentially toxic atmosphere.

It will readily be appreciated that numerous modifications may be made to the monitor shown in the drawings without departing from the concept of the present invention. Thus, for example, the motor may have two drive shafts instead of one; the arrangement of components may be altered thereupon to locate the motor between two gearboxes, one connected to the pump and the other to the tape-winding drum. The clutch mechanism 6 may be omitted, or it may be used simply as a convenient way of disconnecting the tape-winding drum from the gearbox 5 to facilitate unwinding of the tape. In addition to, or in place of, the clutch mechanism it may be advantageous to use an intermittent drive, e.g. a Maltese-cross device, between gearbox 5 and the tape-winding drum. Gearbox 5 need not necessarily be driven directly by a rotating shaft and could be replaced, for example, by a ratchet and pawl mechanism for converting the reciprocal pump strokes into a rotary motion to drive the tape-winding drum, or by a digital electronic dividing device wherein electric pulses produced by rotation of the motor shaft are caused to actuate a small stepper motor for advancing the tape-winding mechanism.

The tape-winding drum is preferably made as large as possible so that there is little change in its effective diameter whilst the length of tape used (e.g. 1–20 cm per hour) is wound onto it.

In order to obtain an even density of stain across the width of the tape it is usual, but not essential, that the pair of plates 8 are formed with essentially square or rectangular holes immediately next to the tape.

The plates acting as guides for the tape are usually made flat but could have mating cylindrically-curved sections if desired.

Where it is necessary, or desirable, to store the exposed tape on the wind-up drum for examination at a later time, it may be advantageous to interleave the used tape layers as they are wound on to the drum with a second stain-impervious tape (which has not been drawn between the perforated plates).

I claim:

1. A monitor for fluids comprising: a casing; a porous indicator tape within the casing; a diaphragm pump within said casing, said pump having an inlet for drawing a fluid sample from outside the casing through a portion of the tape and into the pump and having a discharge outlet for discharging the fluid sample into the interior of the casing; a transport mechanism within the casing for advancing the tape so as to expose a fresh portion of the tape to the fluid sample; and a single electric motor within the casing for driving both the pump and the tape-transport mechanism.

2. A monitor as in claim 1 including within the casing a battery as power source for said motor.

3. A monitor as in claim 1 wherein said transport advances the tape intermittently.

4. A monitor as in claim 1 which is a portable personal monitor for carrying in a pocket or clipping on to clothing.

* * * * *